United States Patent [19]
Yamauchi et al.

[11] Patent Number: 5,932,142
[45] Date of Patent: Aug. 3, 1999

[54] BENZOTRIAZOLYL-ALKYLENE BISPHENOL COMPOUNDS, PROCESS FOR THEIR PREPARATION, AND STABILIZED ORGANIC MATERIALS CONTAINING THEM

[75] Inventors: Toshiyuki Yamauchi, Tokyo; Eisuke Kanagawa, Kitamoto; Hideo Aoki; Kazuyuki Ishihara, both of Toda, all of Japan

[73] Assignee: Johoku Chemical Co., Ltd., Tokyo, Japan

[21] Appl. No.: 08/986,797

[22] Filed: Dec. 8, 1997

[30] Foreign Application Priority Data

Dec. 12, 1996  [JP]  Japan ................................ 8-332397

[51] Int. Cl.$^6$ .......................... C09K 15/08; C09K 15/16; C09K 15/24; C07D 249/20
[52] U.S. Cl. .......................... 252/401; 252/404; 548/259; 548/260
[58] Field of Search .................... 548/259, 260; 252/401, 404

[56] References Cited

U.S. PATENT DOCUMENTS

| | | | |
|---|---|---|---|
| 4,937,348 | 6/1990 | Kubota | 548/259 |
| 5,229,521 | 7/1993 | Luisoli et al. | 548/260 |
| 5,387,691 | 2/1995 | Falk et al. | 548/257 |
| 5,439,955 | 8/1995 | Falk et al. | 524/91 |

FOREIGN PATENT DOCUMENTS

| | | |
|---|---|---|
| 157761 | 1/1974 | Czechoslovakia . |
| 0180993A2 | 5/1986 | European Pat. Off. . |
| 0490815A1 | 6/1992 | European Pat. Off. . |
| 0613891A1 | 9/1994 | European Pat. Off. . |

*Primary Examiner*—Johann Richter
*Assistant Examiner*—Jane Oswecki
*Attorney, Agent, or Firm*—Birch, Stewart, Kolasch & Birch, LLP

[57] ABSTRACT

A process for preparing benzotriazolyl-alkylene bisphenol compounds which comprises reacting a 2-hydroxyphenylbenzotriazole and a 2,4-substituted phenol with an aldehyde in the presence of a basic catalyst and an amine compound; benzotriazolyl-alkylene bisphenol compounds obtained by the process; and stabilized organic materials containing the resulting benzotriazolyl-alkylene bisphenol compounds in an amount of 0.01–10 percent by weight. It is possible to prepare the benzotriazolyl-alkylene bisphenol compounds at a high yield, and organic materials can be effectively stabilized with the resulting compounds.

12 Claims, No Drawings

BENZOTRIAZOLYL-ALKYLENE BISPHENOL COMPOUNDS, PROCESS FOR THEIR PREPARATION, AND STABILIZED ORGANIC MATERIALS CONTAINING THEM

BACKGROUND OF THE INVENTION

1. Field of the Invention

The present invention relates to benzotriazolyl-alkylene bisphenol compounds which function as both light stabilizing agents and antioxidants, to a process for their preparation, and to organic materials stabilized by those compounds.

2. Description of the Related Art 2-hydroxyphenylbenzotriazole compounds are known as light stabilizers for synthetic resins and the like, but because these compounds are of lower molecular weight than the compounds of the invention to be described hereunder, and thus undergo volatilization during working of resins and with the passage of time, they have not been able to stabilize organic materials for extended periods. Also, antioxidants consisting mainly of alkyl-substituted phenols, represented by 2,6-di-tert.-butyl-p-cresol, as well, have been unable to provide long-term stabilization of organic materials for the same reason.

Czechoslovakian Patent No. 157,761 discloses preparation of benzotriazolyl-alkylene bisphenol compounds by a process involving synthesis of the corresponding substituted 2,2'-methylenebisphenol, coupling the bisphenol compound with o-nitrobenzene diazonium salt, and then reducing and cyclizing it by common methods. However, this patent does not disclose the yields, nor have the present inventors been able to confirm production of the desired compounds by reproducing the examples or carrying out the synthesis experiments. The process is therefore deemed to be completely impractical.

SUMMARY OF THE INVENTION

It is the major object of the present invention to provide a process capable of preparing benzotriazolyl-alkylene bisphenol compounds at a high yield.

As a result of much diligent research, the present inventors have accomplished the present invention after finding that benzotriazolyl-alkylene bisphenol compounds can be prepared, at a high yield, by reacting 2-hydroxyphenylbenzotriazoles and 2,4-substituted phenols with aldehydes in the presence of basic catalysts and amines, that the resulting compounds have high lipophilicity and satisfactory resistance to volatilization, and that organic materials stabilized with such compounds are effectively protected even when continuously exposed for long periods to the action of outside air and light.

According to the present invention, therefore, there is provided a process for preparing a benzotriazolyl-alkylene bisphenol compound represented by general formula (3):

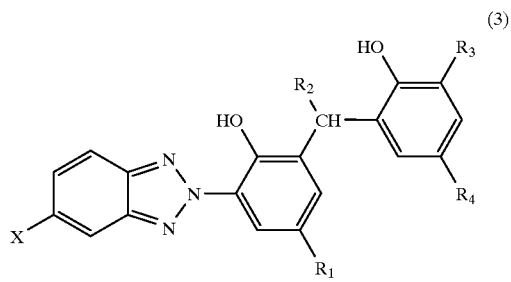

wherein X represents hydrogen, a halogen, or an alkyl, cycloalkyl, alkoxy or alkylaryl group, $R_1$ represents an alkyl, cycloalkyl, aryl, alkoxy or arylalkyl group, $R_2$ represents hydrogen or an alkyl or aryl group, and $R_3$ and $R_4$ may be the same or different and each represent an alkyl, cycloalkyl, aryl or alkylaryl group, which process comprises reacting a 2-hydroxyphenylbenzotriazole represented by general formula (1)

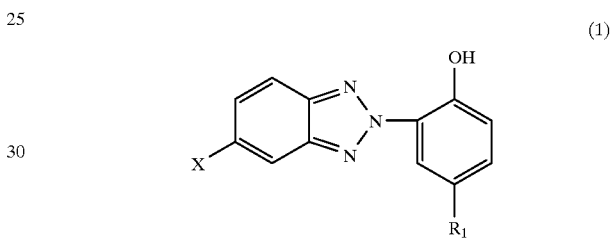

wherein X and $R_1$ are as defined above, and a 2,4-substituted phenol represented by general formula (2):

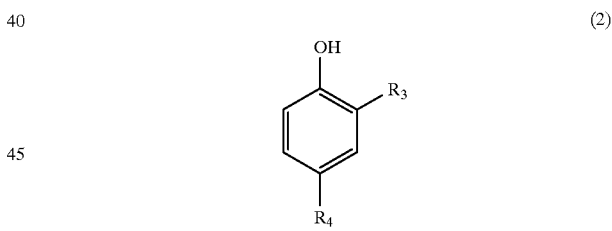

wherein $R_3$ and $R_4$ are as defined above, with an aldehyde selected from the group consisting of formaldehyde, paraformaldehyde, trioxane, tetraoxymethylene, alkylaldehyde and arylaldehyde, in the presence of a basic catalyst and an amine compound.

According to the present invention there is further provided a benzotriazolyl-alkylene bisphenol compound represented by the aforementioned general formula (3) which is prepared by the process described above, and a stabilized organic material containing the compound in an amount of 0.01–10 percent by weight.

Among the compounds represented by the aforementioned general formula (3), those compounds which are represented by the following general formula (4):

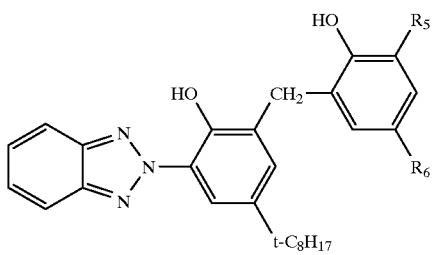

(4)

wherein $R_5$ and $R_6$ may be the same or different and each represents an alkyl group with 1–8 carbon atoms, are novel compounds which have not hitherto been described in literature, and are particularly effective for the stabilization of organic materials.

DESCRIPTION OF THE PREFERRED EMBODIMENTS

The aldehyde used for the process of the invention is selected from the group consisting of formaldehyde, paraformaldehyde, trioxane, tetraoxymethylene, alkylaldehyde and arylaldehyde.

The basic catalyst used may be an alkali metal, alkaline earth metal, or a hydroxide, oxide, hydride, carbonate, amide or alcoholate thereof.

The reaction may also be conducted in the absence of a solvent. If a solvent is used it may be an organic solvent, with no restrictions other than that the organic solvent must not react with the reactants.

As useful amine compounds according to the invention there may be mentioned monoalkyl($C_{1-28}$)amines, monoalkenyl($C_{3-28}$)amines, dialkyl($C_{1-28}$)amines, dialkenyl ($C_{3-28}$) amines, monohydroxyalkyl($C_{1-28}$ )amines, monohydroxyalkenyl($C_{3-28}$)amines, dihydroxyalkyl($C_{1-28}$) amines, dihydroxyalkenyl($C_{3-288}$)amines, 2-amino-2-hydroxymethyl-1,3-propanediol, 2-amino-2-methylpropane-1,3-diol, 2-amino-2-ethyl-1,3-propanediol, alkyl($C_{1-28}$)alkenyl($C_{1-28}$)amines, alkyl($C_{1-28}$)hydroxyalkyl ($C_{1-28}$)amines, alkenyl($C_{3-28}$) hydroxyalkyl($C_{1-28}$)amines, alkyl($C_{1-28}$)hydroxyalkenyl($C_{3-28}$) amines, alkenyl($C_{3-28}$) hydroxyalkenyl($C_{3-28}$,)amines, hydroxyalkyl($C_{1-28}$) hydroxyalkenyl($C_{3-28}$)amines, aniline, diphenylamine, cyclohexylamine, 2-methylcyclohexylamine, cyclohexyldodecylamine, N-alkyl($C_{1-28}$)cyclohexylamines, N-alkenyl($C_{3-28}$) cyclohexylamines and dicyclohexylamine. Particularly preferred among these are alkanolamines (or amino alcohols) such as monoethanolamine, monopropanolamine, monobutanolamine, diethanolamine, dipropanolamine and dibutanolamine.

The benzotriazolyl-alkylene bisphenol compounds of the invention are useful as light stabilizers and antioxidants for organic materials such as resins, fibers, rubber, waxes, paints, fats and oils, cosmetics, inks, heat-sensitive materials, pressure-sensitive materials, light-sensitive materials and the like.

A compound of the invention is generally to be used in an amount of 0.01–10 wt %, and preferably 0.05–2 wt %, with respect to the organic material. For laminated materials, it may be used at a high concentration of 2–10 wt % in only the uppermost layer.

Examples of suitable organic materials include, but are not limited to, homopolymers of olefin and diolefin, such as polyethylene, polypropylene, 1-polybutene, poly-4-methylpentene-1 and 1,2-polybutadiene; copolymers of olefins or olefins and other monomers, such as ethylene-propylene copolymer, ethylene-butene copolymer, ethylene-hexene copolymer, ethylene-4-methylpentene-1 copolymer, ethylene-octene-1 copolymer, ethylene-vinyl acetate copolymer, ethylene-vinylsilane copolymer, ethylene-ethyl acrylate copolymer, ethylene-acrylic acid copolymer, ethylene-carbon dioxide copolymer, ethylene-vinyl acetate-glycidyl methacrylate terpolymer and ionomers; polymers of styrene and substituted styrene, such as polystyrene, poly-p-methylstyrene and poly-α-methylstyrene; copolymers of styrene and other monomers, such as styrene-methacrylic acid ester copolymer, styrene-acrylonitrile copolymer, styrene-butadiene copolymer, styrene-maleic anhydride copolymer, methacrylic acid ester-butadiene-styrene terpolymer, acrylic acid ester-butadiene-styrene terpolymer, acrylic acid ester-acrylonitrile-styrene terpolymer and acrylonitrile-butadiene-styrene terpolymer; modified polyethylenes such as maleic anhydride-modified polyethylene; halogenated resins, such as polyvinyl chloride, polyvinyl bromide, polyvinyl fluoride, polyvinylidene chloride, chlorinated polyethylene, chlorinated polypropylene, polyvinylidene fluoride, polyvinyl fluoride, chlorinated rubber, vinyl chloride-vinyl acetate copolymer, vinyl chloride-ethylene copolymer, polyfunctional acrylic monomer-vinyl chloride copolymer, (ethylene-vinyl acetate)-vinyl chloride copolymer, acrylonitrile-vinyl chloride copolymer, vinyl chloride-vinylidene chloride copolymer and vinyl chloride-urethane copolymer; polyvinyl acetate; polyvinyl alcohol; polyvinyl butyral; polyvinyl stearate; polyvinyl benzoate; polyvinyl maleate; linear thermoplastic polyesters produced by condensation polymerization of dicarboxylic acids and diols, such as polyethylene terephthalate, polybutylene terephthalate and copolymers including combinations of two or more of terephthalic acid, isophthalic acid, 1,4-butanediol, polyethylene glycol, etc.; straight chain polyesters or polyether esters, such as polytetramethylene ether glycol terephthalate; polyphenylene oxide; polyamides produced by polycondensation of diamines and dicarboxylic acids, polycondensation of aminocarboxylic acids and lactam ring opening polymerization; polycarbonates; polyacetals; polysulfones; polyether sulfones; polyether ketones; polyurethanes obtained by reaction of polyisocyanate compounds with polyols; methacrylic resins; polyacrylonitrile; petroleum resins; coumarone resins; fibrous resins; resins obtained by addition condensation of formaldehyde with various phenols, such as phenolic resins, cresol resins, xylenol resins, p-t-butylphenol resins, p-phenylphenol resins and resorcinol resins; urea resins and melamine resins; epoxy resins; unsaturated polyester resins obtained by polycondensation reaction of polyhydric alcohols with unsaturated polybasic acids containing reactive double bonds; silicone resins; natural polymers, such as cellulose, cellulose acetate, cellulose propionate, cellulose butyrate, methylcellulose and gelatin; natural rubber; synthetic isoprene rubber; ethylene-propylene rubber; butyl rubber; chloroprene rubber; polysulfide rubber; acrylic rubber; urethane rubber; chlorosulfonated polyethylene; epichlorohydrin rubber; ethylene-acrylic rubber; ethylene-ethyl acetate elastomer; isobutylene rubber; butadiene rubber; acrylonitrile-butadiene rubber; styrene-butadiene rubber, and other polymeric substances and their blends, natural fats and oils, synthetic ester oils, mineral oils, and the like.

The compounds of the invention may be combined with organic materials by commonly employed processes.

The organic materials which are stabilized by the compounds of the invention may also contain, as desired, commonly used additives, particularly antioxidants, light stabilizers and mixtures thereof.

Examples of such additives include antioxidants such as phenol-based, amine-based, sulfur-based and phosphorous-based antioxidants, and light stabilizers such as salicylic acid-based, benzophenone-based, benzotriazole-based, cyanoacrylate-based, acrylonitrile-based, metal complex nickel-based, cobalt-based and hindered amine-based light stabilizers.

Other additives which may be used include plasticizers, metal inactivators, lubricants, emulsifying agents, fillers, foaming agents, colorants, fluorescent sensitizers, flame retardants and antistatic agents.

The present invention will now be further illustrated by way of examples, with the understanding that the invention is in no way limited by these examples. All of the products in the following synthesis examples were subjected to purification, but such purification is not necessarily required in practice.

EXAMPLE 1

Synthesis of 6-(2-benzotriazolyl)-4-tert.-octyl-6'-tert.-butyl-4'-methyl-2,2'-methylene bisphenol A mixture of 32.3 g of 2-benzotriazolyl-4-tert.-octyl phenol, 16.4 g of 2-tert.-butyl-4-methyl phenol, 18.1 g of dibutylamine, 0.7 g of sodium hydroxide, 3.9 g of paraformaldehyde, 39 g of n-butanol and 150 g of 1,2,4-trimethylbenzene was heated to gradually raise the temperature, and the reaction was carried out for 10 hours at 160–170° C. while recovering the water generated by the reaction together with the n-butanol. The reaction solution was washed with acidic water, and then with water. Next, 46 g of the crude product (92% yield) obtained by recovering the 1,2,4-trimethylbenzene under reduced pressure was recrystallized with isopropyl alcohol to give a purified white powder with a melting point of 148° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 76.9 | 76.9 |
| Hydrogen | 8.3 | 8.4 |
| Nitrogen | 8.4 | 8.5 |
| Oxygen | 6.4 | 6.2 |

EXAMPLE 2

Synthesis of 6-(2-benzotriazolyl)-4-tert.-octyl-6'-tert.-butyl-4'-methyl-2,2'-methylene bisphenol A mixture of 32.3 g of 2-benzotriazolyl-4-tert.-octyl phenol, 16.4 g of 2-tert.-butyl-4-methyl phenol, 8.5 g of monoethanolamine, 2.8 g of sodium hydroxide, 3.9 g of paraformaldehyde and 104 g of n-butanol was heated to gradually raise the temperature, and the reaction was carried out for one hour at 180–190° C. while recovering the water generated by the reaction together with the n-butanol. After adding 104 g of toluene to the reaction solution to dissolve the reaction product, the toluene layer was washed with acidic water and then with water. Next, 47 g of the crude product (94% yield) obtained by recovering the toluene under reduced pressure was recrystallized with isopropyl alcohol to give a purified white powder with a melting point of 148° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 76.9 | 76.8 |
| Hydrogen | 8.3 | 8.2 |
| Nitrogen | 8.4 | 8.6 |
| Oxygen | 6.4 | 6.4 |

EXAMPLE 3

Synthesis of 6-(2-benzotriazolyl)-4-tert.-octyl-4',6'-di-tert.-butyl-2,2'-methylene bisphenol The same procedure was carried out as in Example 1, except that the 16.4 g of 2-tert.-butyl-4-methyl phenol was replaced with 20.6 g of 2,4-di-tert.-butyl phenol.

A 50 g portion of the resulting crude product (92% yield) was recrystallized with isopropyl alcohol to give a purified white powder with a melting point of 137° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 77.6 | 77.7 |
| Hydrogen | 8.7 | 8.8 |
| Nitrogen | 7.8 | 7.8 |
| Oxygen | 5.9 | 5.7 |

EXAMPLE 4

Synthesis of 6-(2-benzotriazolyl)-4-tert.-octyl-4',6'-di-tert.-butyl-2,2'-methylene bisphenol The same procedure was carried out as in Example 2, except that the 16.4 g of 2-tert.-butyl-4-methyl phenol and 8.5 g of monoethanolamine were replaced with 20.6 g of 2,4-di-tert.-butyl phenol and 42.5 g of diethanolamine, respectively.

A 51 g portion of the resulting crude product (94% yield) was recrystallized with isopropyl alcohol to give a purified white powder with a melting point of 137° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 77.6 | 77.7 |
| Hydrogen | 8.7 | 8.6 |
| Nitrogen | 7.8 | 7.8 |
| Oxygen | 5.9 | 5.9 |

EXAMPLE 5

Synthesis of 6-(2-benzotriazolyl)-4-tert.-octyl- 4', 6'-di-tert.-amyl-2,2'-methylene bisphenol The same procedure was carried out as in Example 1, except that the 16.4 g of 2-tert.-butyl-4-methyl phenol was replaced with 23.4 g of 2,4-di-tert.-amyl phenol.

A 52 g portion of the resulting crude product (91% yield) was recrystallized with isopropyl alcohol to give a purified white powder with a melting point of 80° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 78.0 | 78.0 |
| Hydrogen | 9.0 | 8.8 |
| Nitrogen | 7.4 | 7.6 |
| Oxygen | 5.6 | 5.6 |

EXAMPLE 6

Synthesis of 6-(2-benzotriazolyl)-4-tert.-octyl-4', 6'-di-tert.-amyl-2,2'-methylene bisphenol The same procedure was carried out as in Example 2, except that the 16.4 g of 2-tert.-butyl-4-methyl phenol was replaced with 23.4 g of 2,4-di-tert.-amyl phenol.

A 53 g portion of the resulting crude product (93% yield) was recrystallized with isopropyl alcohol to give a purified white powder with a melting point of 80° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 78.0 | 77.9 |
| Hydrogen | 9.0 | 9.1 |
| Nitrogen | 7.4 | 7.4 |
| Oxygen | 5.6 | 5.6 |

EXAMPLE 7

Synthesis of 6-(2-benzotriazolyl)-4-tert.-octyl-4', 6'-di-tert.-octyl-2,2'-methylene bisphenol The same procedure was carried out as in Example 1, except that the 16.4 g of 2-tert.-butyl-4-methyl phenol was replaced with 31.9 g of 2,4-di-tert.-octyl phenol.

A 59 g portion of the resulting crude product (90% yield) was recrystallized with isopropyl alcohol to give a purified white powder with a melting point of 174° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 79.0 | 78.9 |
| Hydrogen | 9.7 | 9.8 |
| Nitrogen | 6.4 | 6.5 |
| Oxygen | 4.9 | 4.8 |

EXAMPLE 8

Synthesis of 6-(2-benzotriazolyl)-4-tert.-octyl-4', 6'-di-tert.-octyl-2,2'-methylene bisphenol The same procedure was carried out as in Example 2, except that the 16.4 g of 2-tert.-butyl-4-methyl phenol was replaced with 31.9 g of 2,4-di-tert.-octyl phenol.

A 60 g portion of the resulting crude product (92% yield) was recrystallized with isopropyl alcohol to give a purified white powder with a melting point of 174° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 79.0 | 79.0 |
| Hydrogen | 9.7 | 9.5 |
| Nitrogen | 6.4 | 6.5 |
| Oxygen | 4.9 | 5.0 |

EXAMPLE 9

Synthesis of 6-(2-benzotriazolyl)-4-tert.-butyl-6'-tert.-butyl-4'-methyl-2,2'-methylene bisphenol The same procedure was carried out as in Example 2, except that the 32.3 g of 2-benzotriazolyl-4-tert.-octyl phenol was replaced with 26.7 g of 2-benzotriazolyl-4-tert.-butyl phenol.

A 41 g portion of the resulting crude product (93% yield) was recrystallized with isopropyl alcohol to give a purified white powder with a melting point of 175° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 75.8 | 75.6 |
| Hydrogen | 7.5 | 7.6 |
| Nitrogen | 9.5 | 9.6 |
| Oxygen | 7.2 | 7.2 |

EXAMPLE 10

Synthesis of 6-(2-benzotriazolyl)-4-tert.-butyl-4', 6'-di-tert.-butyl-2,2'-methylene bisphenol The same procedure was carried out as in Example 2, except that the 32.3 g of 2-benzotriazolyl-4-tert.-octyl phenol, 16.4 g of 2-tert.-butyl-4-methyl phenol and 8.5 g of monoethanolamine were replaced with 26.7 g of 2-benzotriazolyl -4-tert.-butyl phenol, 20.6 g of 2,4-di-tert. -butyl phenol and 42.5 g of diethanolamine, respectively.

A 45 g portion of the resulting crude product (92% yield) was recrystallized with isopropyl alcohol to give a purified white powder with a melting point of 208° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 76.7 | 76.7 |
| Hydrogen | 8.1 | 7.9 |
| Nitrogen | 8.6 | 8.6 |
| Oxygen | 6.6 | 6.8 |

EXAMPLE 11

Synthesis of 6-(2-benzotriazolyl)-4-tert.-butyl-4', 6'-di-tert.-amyl-2,2'-methylene bisphenol The same procedure was carried out as in Example 2, except that the 32.3 g of 2-benzotriazolyl-4-tert.-octyl phenol and 16.4 g of 2-tert.-butyl-4-methyl phenol were replaced with 26.7 g of 2-benzotriazolyl-4-tert.-butyl phenol and 23.4 g of 2,4-di-tert.-amyl phenol, respectively.

A 48 g portion of the resulting crude product (93% yield) was recrystallized with isopropyl alcohol to give a purified white powder with a melting point of 186° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 77.2 | 77.2 |
| Hydrogen | 8.4 | 8.2 |
| Nitrogen | 8.2 | 8.3 |
| Oxygen | 6.2 | 6.3 |

EXAMPLE 12

Synthesis of 6-(2-benzotriazolyl)-4-tert.-butyl-4', 6'-di-tert.-octyl-2,2'-methylene bisphenol The same procedure was carried out as in Example 2, except that the 32.3 g of 2-benzotriazolyl-4-tert.-octyl phenol and 16.4 g of 2-tert.-butyl-4-methyl phenol were replaced with 26.7 g of 2-benzotriazolyl-4-tert.-butyl phenol and 31.9 g of 2,4-di-tert.-octyl phenol, respectively.

A 55 g portion of the resulting crude product (92% yield) was recrystallized with isopropyl alcohol to give a purified white powder with a melting point of 166° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 78.4 | 78.3 |
| Hydrogen | 9.3 | 9.5 |
| Nitrogen | 7.0 | 6.9 |
| Oxygen | 5.3 | 5.3 |

EXAMPLE 13

Synthesis of 6-(2-benzotriazolyl)-4-methyl-6'-tert.-butyl -4'-methyl-2,2'-methylene bisphenol The same procedure was carried out as in Example 2, except that the 32.3 g of 2-benzotriazolyl-4-tert.-octyl phenol was replaced with 22.5 g of 2-benzotriazolyl-4-methyl phenol.

A 38 g portion of the resulting crude product (94% yield) was recrystallized with isopropyl alcohol to give a purified white powder with a melting point of 167° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 74.8 | 74.8 |
| Hydrogen | 6.7 | 6.6 |
| Nitrogen | 10.5 | 10.7 |
| Oxygen | 8.0 | 7.9 |

EXAMPLE 14

Synthesis of 6-(2-benzotriazolyl)-4-methyl-4', 6'-di-tert. -butyl-2,2'-methylene bisphenol The same procedure was carried out as in Example 2, except that the 32.3 g of 2-benzotriazolyl-4-tert.-octyl phenol, 16.4 g of 2-tert.-butyl-4-methyl phenol and 8.5 g of monoethanolamine were replaced with 22.5 g of 2-benzotriazolyl -4-methyl phenol, 20.6 g of 2,4-di-tert.-butyl phenol and 42.5 g of diethanolamine, respectively.

A 41 g portion of the resulting crude product (92% yield) was recrystallized with isopropyl alcohol to give a purified white powder with a melting point of 171° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 75.8 | 75.6 |
| Hydrogen | 7.5 | 7.6 |
| Nitrogen | 9.5 | 9.6 |
| Oxygen | 7.2 | 7.2 |

EXAMPLE 15

Synthesis of 6-(2-benzotriazolyl)-4-methyl-4', 6'-di-tert. -amyl-2,2'-methylene bisphenol The same procedure was carried out as in Example 2, except that the 32.3 g of 2-benzotriazolyl-4-tert.-octyl phenol and 16.4 g of 2-tert.-butyl-4-methyl phenol were replaced with 22.5 g of 2-benzotriazolyl-4-methyl phenol and 23.4 g of 2,4-di-tert.-amyl phenol, respectively.

A 44 g portion of the resulting crude product (93% yield) was recrystallized with isopropyl alcohol to give a purified white powder with a melting point of 116° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 76.4 | 76.3 |
| Hydrogen | 7.9 | 8.1 |
| Nitrogen | 8.9 | 8.9 |
| Oxygen | 6.8 | 6.7 |

EXAMPLE 16

Synthesis of 6-(2-benzotriazolyl)-4-methyl-4', 6'-di-tert. -octyl-2,2'-methylene bisphenol The same procedure was carried out as in Example 2, except that the 32.3 g of 2-benzotriazolyl-4-tert.-octyl phenol and 16.4 g of 2-tert.-butyl-4-methyl phenol were replaced with 22.5 g of 2-benzotriazolyl-4-methyl phenol and 31.9 g of 2,4-di-tert.-octyl phenol, respectively.

A 52 g portion of the resulting crude product (94% yield) was recrystallized with isopropyl alcohol to give a purified white powder with a melting point of 138° C.

The purity of the purified product was 100% as analyzed by liquid chromatography.

The results of C, H, N and O elemental analysis of the purified product were close to calculated values as shown in the following table, thus confirming production of the object compound.

| Element | Calculated (%) | Found (%) |
|---|---|---|
| Carbon | 77.8 | 77.8 |
| Hydrogen | 8.8 | 9.0 |
| Nitrogen | 7.6 | 7.4 |
| Oxygen | 5.8 | 5.8 |

Table 1 below provides a list of the comparison compounds and the compounds of the invention used in the following examples.

TABLE 1

| | Compound name |
|---|---|
| Comparison compound | 2-benzotriazolyl-4-methyl phenol |
| Invention compound 1 | 6-(2-benzotriazolyl)-4-t-butyl-6'-t-butyl-4'-methyl-2,2'-methylene bisphenol |
| Invention compound 2 | 6-(2-benzotriazolyl)-4-t-butyl-4',6'-di-t-butyl-2,2'-methylene bisphenol |
| Invention compound 3 | 6-(2-benzotriazolyl)-4-t-butyl-4',6'-di-t-amyl-2,2'-methylene bisphenol |
| Invention compound 4 | 6-(2-benzotriazolyl)-4-t-butyl-4',6'-di-t-octyl-2,2'-methylene bisphenol |
| Invention compound 5 | 6-(2-benzotriazolyl)-4-t-octyl-6'-t-butyl-4'-methyl-2,2'-methylene bisphenol |
| Invention compound 6 | 6-(2-benzotriazolyl)-4-t-octyl-4',6'-di-t-butyl-2,2'-methylene bisphenol |
| Invention compound 7 | 6-(2-benzotriazolyl)-4-t-octyl-4',6'-di-t-amyl-2,2'-methylene bisphenol |
| Invention compound 8 | 6-(2-benzotriazolyl)-4-t-octyl-4',6'-di-t-octyl-2,2'-methylene bisphenol |
| Invention compound 9 | 6-(2-benzotriazolyl)-4-methyl-4',6'-t-butyl-4'-methyl-2,2'-methylene bisphenol |
| Invention compound 10 | 6-(2-benzotriazolyl)-4-methyl-4',6'-di-t-butyl-2,2'-methylene bisphenol |
| Invention compound 11 | 6-(2-benzotriazolyl)-4-methyl-4',6'-di-t-amyl-2,2'-methylene bisphenol |
| Invention compound 12 | 6-(2-benzotriazolyl)-4-methyl-4',6'-di-t-octyl-2,2'-methylene bisphenol |

EXAMPLE 17

The weight reductions of the invention compounds after heating at 250° C. for 40 minutes were measured with a differential thermogravimetric apparatus in order to determine their resistance to volatilization. The solubilities of the invention compounds in 100 g of xylene at 25° C. were also determined as an index of their compatibility with organic materials. The results are shown in Table 2 below.

TABLE 2

| | Reduction (%) | Solubility (g/100 g xylene, 25°C.) |
|---|---|---|
| Comparison compound | 100 | 7 |
| Invention compound 1 | 9 | 18 |
| Invention compound 2 | 10 | 2 |
| Invention compound 3 | 8 | 8 |
| Invention compound 4 | 6 | 5 |
| Invention compound 5 | 8 | 29 |
| Invention compound 6 | 7 | 35 |
| Invention compound 7 | 7 | 29 |
| Invention compound 8 | 5 | 14 |
| Invention compound 9 | 12 | 12 |
| Invention compound 10 | 15 | 20 |

TABLE 2-continued

|  | Reduction (%) | Solubility (g/100 g xylene, 25°C.) |
|---|---|---|
| Invention compound 11 | 10 | 61 |
| Invention compound 12 | 10 | 13 |

EXAMPLE 18

In order to determine the excellent light stabilizing effects of the invention compounds, different non-stabilized resins containing no light stabilizers were used to prepare pressed sheets of 150 mm length×70 mm width×0.5 mm thickness with the compositions listed in Table 3 below, and the sheets were tested using a Sunshine carbon-arc lamp weathering tester (product of Suga Experimental Instruments, KK.). For the polycarbonate of Example 18-4, the test was made using the super accelerated weathering tester: Eye Super UV Tester (product of Dainihon Plastics, KK.). The results are given in Table 4 below.

TABLE 3

|  | Example 18-1 | Example 18-2 | Example 18-3 | Example 18-4 |
|---|---|---|---|---|
| Polypropylene | 100 wt pts | — | — | — |
| Polyvinyl chloride | — | 100 wt pts | — | — |
| Polystyrene | — | — | 100 wt pts | — |
| Polycarbonate | — | — | — | 100 wt pts |
| Stabilizer | 0.2 wt pt | 0.3 wt pt | 0.2 wt pt | 10 wt pts |

TABLE 4

Evaluation: x (discoloration), Δ (slight discoloration),
o (very slight discoloration), ⊚ (no discoloration)

| Stabilizer | Example 18-1 Testing time: 500 hrs | Example 18-2 Testing time: 800 hrs | Example 18-3 Testing time: 500 hrs | Example 18-4 Testing time: 100 hrs |
|---|---|---|---|---|
| Comparison compound | x | x | x | x |
| Invention compound 1 | o | o | o | o |
| Invention compound 2 | o | o | o | o |
| Invention compound 3 | o | o | o | o |
| Invention compound 4 | o | o | o | o |
| Invention compound 5 | ⊚ | ⊚ | ⊚ | ⊚ |
| Invention compound 6 | ⊚ | ⊚ | ⊚ | ⊚ |
| Invention compound 7 | ⊚ | ⊚ | ⊚ | ⊚ |
| Invention compound 8 | ⊚ | ⊚ | ⊚ | ⊚ |
| Invention compound 9 | o | o | o | Δ |
| Invention compound 10 | o | o | o | Δ |
| Invention compound 11 | o | o | o | Δ |
| Invention compound 12 | o | o | o | Δ |

EXAMPLE 19

In order to determine the excellent light stabilizing effects of the invention compounds, non-stabilized chloroprene containing no light stabilizer was used to prepare the sample solution specified below which was applied three times, as a resin, onto a microscope glass slide (76×26 mm) to a dry weight of 90 g/m². After the application, the slide was air-dried for 2 days in a dark area at room temperature to make a test piece. The test piece was subjected to a sunlight weather resistance for 3 days. The results are given in Table 5. To determine the antioxidizing effect, a test piece prepared in the same manner using non-stabilized chloroprene containing no antioxidant was subjected to a heat resistance test by heating at 130° C. for 10 hours using a gear aging tester (product of Toyo Precision Instruments, KK.). The results are given in Table 6.

Sample solution
Non-stabilized chloroprene 10 pts. by wt.
Toluene 57 pts. by wt.
Stabilizer 0.2 pt. by wt.

TABLE 5

Evaluation: x (discoloration), Δ (slight discoloration),
o (very slight discoloration), ⊚ (no discoloration)

| Stabilizer | Weather resistance |
|---|---|
| Comparison compound | x |
| Invention compound 1 | o |
| Invention compound 2 | o |
| Invention compound 3 | o |
| Invention compound 4 | o |
| Invention compound 5 | ⊚ |
| Invention compound 6 | ⊚ |
| Invention compound 7 | ⊚ |
| Invention compound 8 | ⊚ |
| Invention compound 9 | o |
| Invention compound 10 | Δ |
| Invention compound 11 | Δ |
| Invention compound 12 | Δ |

TABLE 6

| Stabilizer | 0.5 hr | 1 hr | 10 hrs |
|---|---|---|---|
| None | coloration | browning | browning |
| 2,6-di-t-butyl-p-cresol | slight coloration | browning | browning |
| Invention compound 1 | no coloration | no coloration | no coloration |
| Invention compound 2 | no coloration | no coloration | slight coloration |
| Invention compound 3 | no coloration | no coloration | slight coloration |
| Invention compound 4 | no coloration | no coloration | slight coloration |
| Invention compound 5 | no coloration | no coloration | no coloration |
| Invention compound 6 | no coloration | no coloration | slight coloration |
| Invention compound 7 | no coloration | no coloration | slight coloration |
| Invention compound 8 | no coloration | no coloration | slight coloration |
| Invention compound 9 | no coloration | no coloration | no coloration |
| Invention compound 10 | no coloration | no coloration | slight coloration |

TABLE 6-continued

| Stabilizer | Testing time | | |
|---|---|---|---|
| | 0.5 hr | 1 hr | 10 hrs |
| Invention compound 11 | no coloration | no coloration | slight coloration |
| Invention compound 12 | no coloration | no coloration | slight coloration |

Table 2 shows that the compounds of the invention have excellent resistance to volatilization and high lipophilicity, Tables 4 and 5 show that they provide a considerable light stabilizing effect, and Table 6 shows that they have better antioxidizing actions than the commonly used antioxidant 2,6-di-tert.-butyl-p-cresol; the compounds of the invention, therefore, can very effectively stabilize organic materials.

We claim:

1. A process for preparing a benzotriazolyl-alkylene bisphenol compound represented by general formula (3):

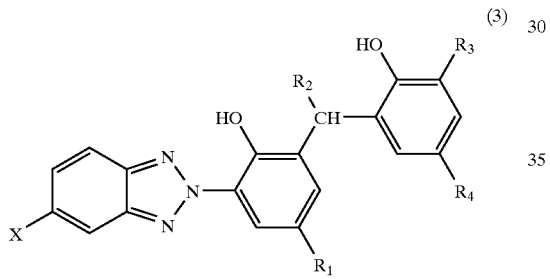

(3)

wherein X represents hydrogen, a halogen, or an alkyl, cycloalkyl, alkoxy or alkylaryl group, $R_1$ represents an alkyl, cycloalkyl, aryl, alkoxy or arylalkyl group, $R_2$ represents hydrogen or an alkyl or aryl group, and $R_3$ and $R_4$ may be the same or different and each represent an alkyl, cycloalkyl, aryl or alkylaryl group, which process comprises reacting a 2-hydroxyphenylbenzotriazole represented by general formula (1):

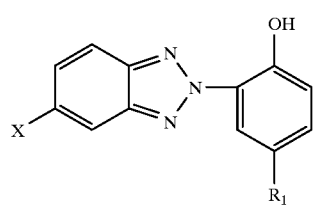

(1)

wherein X and $R_1$ are as defined above, and a 2,4-substituted phenol represented by general formula (2):

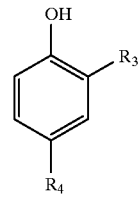

(2)

wherein $R_3$ and $R_4$ are as defined above, with an aldehyde selected from the group consisting of formaldehyde, paraformaldehyde, trioxane, tetraoxymethylene, alkylaldehyde and arylaldehyde, in the presence of a basic catalyst and an amine compound.

2. A benzotriazolyl-alkylene bisphenol compound represented by the following general formula (4):

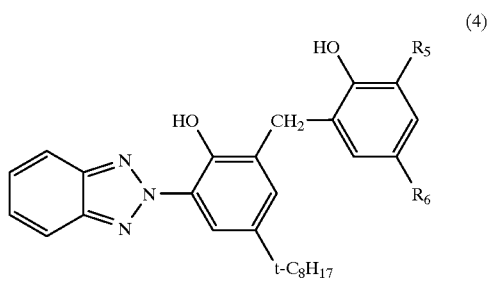

(4)

wherein $R_5$ and $R_6$ may be the same or different and each represents an alkyl group with 1–8 carbon atoms.

3. A stabilized organic material containing a benzotriazolyl-alkylene bisphenol compound of formula (4) according to claim 2, in an amount of 0.01–10 percent by weight.

4. A method of stabilizing an organic material against light, comprising mixing the compound of claim 2 in the organic material.

5. A method of preventing oxidation of an organic material, comprising mixing the compound of claim 2 in the organic material.

6. The method according to claim 4, wherein said organic material is a resin, a fiber, a rubber, a wax, a paint, a fat, an oil, a cosmetic, an ink, a heat-sensitive material, a pressure-sensitive material, or a light-sensitive material.

7. The method according to claim 5, wherein said organic material is a resin, a fiber, a rubber, a wax, a paint, a fat, an oil, a cosmetic, an ink, a heat-sensitive material, a pressure-sensitive material, or a light-sensitive material.

8. The organic material according to claim 3, wherein said organic material is a resin, a fiber, a rubber, a wax, a paint, a fat, an oil, a cosmetic, an ink, a heat-sensitive material, a pressure-sensitive material, or a light-sensitive material.

9. The compound according to claim 2, wherein said compound is 6-(2-benzotriazolyl)-4-t-octyl-6'-t-butyl -4'-methyl -2,2'-methylene bisphenol.

10. The compound according to claim 2, wherein said compound is 6-(2-benzotriazolyl)-4-t-octyl-4',6'-di-t-butyl-2,2'-methylene bisphenol.

11. The compound according to claim 2, wherein said compound is 6-(2-benzotriazolyl)-4-t-octyl -4',6'-di -t-amyl-2,2'-methylene bisphenol.

12. The compound according to claim 2, wherein said compound is 6-(2-benzotriazolyl)-4-t-octyl-4',6'-di-t-octyl-2,2'-methylene bisphenol.

\* \* \* \* \*